(12) United States Patent
Fischer et al.

(10) Patent No.: US 9,403,726 B2
(45) Date of Patent: Aug. 2, 2016

(54) LIGHT-CURING CERAMIC SLIPS FOR THE STEREOLITHOGRAPHIC PREPARATION OF HIGH-STRENGTH CERAMICS

(71) Applicant: Ivoclar Vivadent AG, Schaan (LI)

(72) Inventors: Urs Karl Fischer, Arbon (CH); Norbert Moszner, Mauren (LI); Volker Rheinberger, Vaduz (LI); Wolfgang Wachter, Schaan (LI); Johannes Homa, Vienna (AT); Werner Längle, Frastanz (AT)

(73) Assignee: Ivoclar Vivadent AG, Schaan (LI)

( * ) Notice: Subject to any disclaimer, the term of this patent is extended or adjusted under 35 U.S.C. 154(b) by 126 days.

(21) Appl. No.: 14/200,323

(22) Filed: Mar. 7, 2014

(65) Prior Publication Data

US 2014/0183799 A1 Jul. 3, 2014

Related U.S. Application Data

(62) Division of application No. 13/172,955, filed on Jun. 30, 2011, now abandoned.

(30) Foreign Application Priority Data

Jul. 8, 2010 (EP) .................................. 10007066

(51) Int. Cl.
| | | |
|---|---|---|
| C04B 35/00 | (2006.01) |
| C04B 35/111 | (2006.01) |
| C04B 35/053 | (2006.01) |
| C04B 35/64 | (2006.01) |
| C08L 33/04 | (2006.01) |
| A61K 6/02 | (2006.01) |
| A61K 6/027 | (2006.01) |
| A61K 6/083 | (2006.01) |
| C04B 35/486 | (2006.01) |
| C04B 35/488 | (2006.01) |
| C04B 35/626 | (2006.01) |
| C04B 35/632 | (2006.01) |
| C04B 35/634 | (2006.01) |

(52) U.S. Cl.
CPC ................ *C04B 35/64* (2013.01); *A61K 6/024* (2013.01); *A61K 6/025* (2013.01); *A61K 6/0215* (2013.01); *A61K 6/0273* (2013.01); *A61K 6/083* (2013.01); *C04B 35/111* (2013.01); *C04B 35/486* (2013.01); *C04B 35/4885* (2013.01); *C04B 35/6263* (2013.01); *C04B 35/6264* (2013.01); *C04B 35/6325* (2013.01); *C04B 35/6346* (2013.01); *C04B 35/63424* (2013.01); *C04B 35/63488* (2013.01); *C04B 2235/3206* (2013.01); *C04B 2235/3208* (2013.01); *C04B 2235/3225* (2013.01); *C04B 2235/3229* (2013.01); *C04B 2235/44* (2013.01); *C04B 2235/449* (2013.01); *C04B 2235/6026* (2013.01); *C04B 2235/96* (2013.01); *C04B 2235/9661* (2013.01)

(58) Field of Classification Search
CPC ..... A61K 6/0125; A61K 6/024; A61K 6/025; A61K 6/0273; A61K 6/083; C04B 35/64; C04B 35/111; C04B 35/486; C04B 35/4885; C04B 35/6263; C04B 35/6264; C04B 35/6325; C04B 35/63424; C04B 35/6346; C04B 35/63488; C08L 33/00
See application file for complete search history.

(56) References Cited

U.S. PATENT DOCUMENTS

| | | | |
|---|---|---|---|
| 5,496,682 A | 3/1996 | Quadir et al. |
| 5,768,134 A | 6/1998 | Swaelens et al. |
| 6,117,612 A | 9/2000 | Halloran et al. |
| 2002/0167100 A1 | 11/2002 | Moszner et al. |
| 2002/0187458 A1 | 12/2002 | Dolabdjian et al. |
| 2003/0114554 A1 | 6/2003 | Ario et al. |
| 2005/0090575 A1 | 4/2005 | Chaput et al. |
| 2007/0254979 A1* | 11/2007 | Salz ..................... A61K 6/0017 523/116 |
| 2008/0206715 A1 | 8/2008 | Kawamoto et al. |
| 2009/0176194 A1 | 7/2009 | Qian |
| 2010/0029801 A1* | 2/2010 | Moszner ................. G03F 7/027 522/167 |

FOREIGN PATENT DOCUMENTS

| | | |
|---|---|---|
| DE | 19938463 A1 | 2/2001 |
| DE | 19950284 A1 | 4/2001 |
| DE | 102005058116 A1 | 3/2007 |
| WO | 97/29901 | 8/1997 |

OTHER PUBLICATIONS

Gebhardt, A., Vision Rapid Prototyping, Ber. DGK, 2006, vol. 83, No. 13, pp. 7-12.
Gebhardt, A., Generative Fertigugsanlagen für Rapid Prototyping, Direct Tooling und Direct Manufacturing, Generative Fertigungsverfahren,3rd edition, Carl Hanser Verlag, Munich 2007, p. 77 et seq.

(Continued)

*Primary Examiner* — Karuna P Reddy
(74) *Attorney, Agent, or Firm* — Ann M. Knab; Thad McMurray (57) ABSTRACT

A process for the preparation of a ceramic or glass ceramic shaped article using stereolithography and using a slip based on a radically polymerizable binder, polymerization initiator and filler, which comprises (A) at least one acidic monomer of general formula I

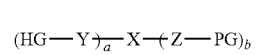

Formula I (B) photoinitiator, and (C) ceramic and/or glass ceramic particles.

22 Claims, 1 Drawing Sheet

(56) References Cited

OTHER PUBLICATIONS

Moreno, R., The Role of Slip Additives in Tape Casting Technology: Part II—Binders and Plasticizers, Amer. Ger. Soc. Bull., Nov. 1992, vol. 71, No. 11, pp. 1647-1657.

Fouassier, J.P., et al., Radiation Curing in Polymer Science and Technology—vol. II, Photoinitiating Systems, Elsevier Applied Science, 1993, London and New York.

Crivello, J.V., et al., vol. III Photoinitiators for Free Radical Cationic & Anionic Photopolymerization, 2nd Ed., Surface Coatings Technology, 1998, Wiley & Sons, Chichester etc., pp. 229-339.

Otsu, T., et al., Role of Initiator-Transfer Agent-Terminator (Iniferter) in Radical Polymerizations: Polymer Design by Organic Disulfides as Iniferters, Makromol. Chem., Rapid. Commun., 1982, vol. 3, pp. 127-132.

Elias, H.-G., Makromoleküe le, Band 1: Chemische Struktur und Synthesen, 1999, vol. 1, 6th Edition, Wiley-VCH, Weinheim etc., pp. 193-197.

Beil, A., Fertigung von Mikro-Bauteilen mittels Stereolitographie, 2002, VOi-Veriag, Dusseldorf, pp. 3 et seq.

EP Search Report for European Patent Application No. 10007066.3.

\* cited by examiner

US 9,403,726 B2

LIGHT-CURING CERAMIC SLIPS FOR THE STEREOLITHOGRAPHIC PREPARATION OF HIGH-STRENGTH CERAMICS

CROSS-REFERENCE TO RELATED APPLICATIONS

This application is a divisional application of U.S. Ser. No. 13/172,955, filed Jun. 30, 2011, which claims the benefit of European Patent Application No. 10007066.3 filed Jul. 8, 2010, which are hereby incorporated by reference in their entirety.

TECHNICAL FIELD

The present invention relates to light-curing ceramic slips for the stereolithographic preparation of high-strength ceramics, such as ceramic shaped parts or articles, dental inlays, onlays, veneers, crowns, bridges and frameworks.

BACKGROUND

The term "rapid prototyping" (RP) covers generative manufacturing processes in which 3-dimensional models or components are prepared from computer-aided design data (CAD data) (A. Gebhardt, Vision of Rapid Prototyping, Ber. DGK 83 (2006) 7-12). These are processes, such as stereolithography (SL), selective laser sintering (SLS), 3D printing, fused deposition modelling (FDM), ink-jet printing (IJP), 3D plotting, multi-jet modelling (MJM), solid freeform fabrication (SFF), laminated object manufacturing (LOM), laser powder forming (LPF) and direct ceramic jet printing (DCJP), with which models, components or shaped parts can be prepared cheaply even on a small scale (A. Gebhardt, Generative Fertigungsverfahren, 3rd edition, Carl Hanser Verlag, Munich 2007, 77 et seq.). Stereolithography involves RP processes (A. Beil, Fertigung von Mikro-Bauteilen mittels Stereolithographie, Düsseldorf 2002, VDI-Verlag 3 et seq.) in which a shaped part is constructed in layers from a liquid and curable monomer resin on the basis of CAD data.

Stereolithographic processes for the preparation of dental shaped articles, such as inlays, crowns or bridges, are highly advantageous particularly with ceramic materials, because the impression-taking and casting processes and the grinding and milling operations, respectively, which involve considerable manual outlay in the dental laboratory, can thus be greatly simplified and at the same time the large material loss which occurs with non-generative processes can be avoided. As a complete digital process chain is in place today, the standard process steps for the preparation of e.g. multi-unit bridge frameworks (alignment in the articulator, wax modulation, embedding and casting) can be replaced by the digitalization of the model, the virtual design of the dental shaped article and its generative stereolithographic manufacture.

In the stereolithographic preparation of ceramic shaped parts a ceramic green compact is firstly prepared by radiation curing layer-by-layer of a free-flowing ceramic slip which is then sintered after debinding to form a dense ceramic shaped article. The green compact is also referred to as a green body. The term debinding is used to describe the elimination of the binder. In this step, the binder employed is usually removed by heating the green compact to a temperature of about 90° C. to 600° C. It is essential that the formation of cracks and deformations are very largely avoided. The green body becomes the so-called white body as a result of the debinding.

In debinding, purely thermal as well as thermochemical processes take place. Mixtures of water, solvents, polymers, waxes or oils are usually employed as binders in the pressing of ceramic powders. Polypropylene, polyethylene, polyvinyl acetate, polyvinyl alcohol, methylcellulose, polyvinylpyrrolidone, polystyrene or polyethyl methacrylate are most often used as polymers (cf. R. Moreno, Amer. Cer. Soc. Bull. 71 (1992) 1647-1657). These are linear polymers which are broken down more or less easily at increased temperature into volatile components through depolymerization or chain-splitting.

The sintering of the white body takes place in the sintering furnace during high-temperature firing. This results in a compacting and solidifying of the finely-dispersed ceramic powder by exposure to a temperature below the melting temperature of the main components, whereby the porous body becomes smaller and its strength increases.

EP 1 021 997 A2 and US 2005056350 (A1), which is hereby incorporated by reference, describe the use of the laser-sintering process for the preparation of dental restorations. Here, metal powders are sintered in layers using a laser. US DE 101 14 290 A1 and U.S. Pat. No. 6,939,489, which is hereby incorporated by reference, relate to the preparation of dental shaped parts by 3D plotting using materials that are meltable, condensable, curable thermally or with UV or visible light, filled or unfilled. For the preparation of green bodies inorganic pastes are proposed which are composed of glass, glass ceramic or ceramic powder, which is converted into a shapable paste with solvent, binder and plasticizer. The powders used are not surface-modified.

WO 97/29901, which is hereby incorporated by reference, describes a process and an apparatus for the preparation of 3-dimensional components from a liquid, curable medium. The component is constructed in layers by scanning each individual layer with a laser and curing it. The next layer of the curable material is then deposited by means of a coating device and then likewise cured.

A stereolithographic process for the preparation of dental implants is known from WO 95/28688 and U.S. Pat. No. 5,768,134, which is hereby incorporated by reference.

U.S. Pat. No. 5,496,682, which is hereby incorporated by reference, discloses light-curable compositions for the preparation of three-dimensional bodies by stereolithography, which contain 40 to 70 vol.-% ceramic or metal particles, 10 to 35 wt.-% monomer, 1 to 10 wt.-% photoinitiator, 1 to 10 wt.-% dispersant and preferably also solvent, plasticizer and coupling agent.

U.S. Pat. No. 6,117,612, which is hereby incorporated by reference, describes resins for the stereolithographic preparation of sintered ceramic or metal parts. The resins have a viscosity of less than 3000 mPa·s. For their preparation, monomers with a low viscosity are used, preferably in aqueous solution. A high solids content and low viscosity are said to be achieved through the use of dispersants.

DE 10 2005 058 116 A1, which is hereby incorporated by reference, discloses suspensions for the stereolithographic preparation of ceramic implants in the manner described in U.S. Pat. No. 6,117,612, which is hereby incorporated by reference, which do not contain diluents such as water or organic solvents, as the latter are said to increase the viscosity through local evaporation when energy is introduced. The viscosity of the suspension is adjusted to less than 20 Pa·s by varying the concentration of a dispersant. Alkyl ammonium salts of copolymers with acidic groups are used as dispersants, which can also be coated onto the particles of the ceramic powder.

Methods and compositions for the stereolithographic preparation of ceramic components are described in US 2005/

0090575 A1, which is hereby incorporated by reference. It is stated that shaped parts prepared with the liquid materials known from U.S. Pat. No. 5,496,682, which is hereby incorporated by reference, are soft and therefore require an additional curing step in order to avoid deformations during firing, while shaped articles obtained from paste-like materials develop internal stresses during debinding which lead to cracks during sintering. To avoid these problems, plasticizers are used and the quantity of ceramic powder is chosen such that the viscosity of the compositions is at least 10,000 Pa·s.

Compositions curable with visible light and their use for the preparation of dental restorations from plastic materials by RP processes are described in DE 199 38 463 A1 and DE 199 50 284 A1, which are hereby incorporated by reference.

For the preparation of high-strength ceramics, the process chain must be carried out in such a way that cracks, separated layers, pores and other defects or deformations do not occur during the preparation of the green body, brown body and white body. In this regard, the composition and the properties of the radiation-curable slip are of decisive importance. Thus as high as possible a proportion by volume of the ceramic particles in the slip is required in particular for a high density and final strength as well as good accuracy of fit of the ceramic shaped part. Furthermore, a properly adjusted rheology of the slip is a basic requirement for a rapid and problem-free stereolithographic construction of a green body with few defects, wherein however the viscosity and the flow behaviour depend among other things on the size and the content of the ceramic particles in the slip as well as on the type and quantity of added rheology additives.

The stability of the stereolithographically produced green bodies can be improved by using cross-linking monomers. The curing time which is required to obtain a stable solid can thereby be significantly shortened. However, at the same time, the polymer network that forms also displays a much higher thermal stability compared with linear polymers, which adversely affects the debinding process. Moreover, the polymerization shrinkage increases with the functionality of the monomers which can lead to considerable shrinkage stresses. As a result, green bodies, brown bodies and sintered white bodies which have porosities and defects are often obtained even during optimized processing methods. A particular problem with the stereolithographic preparation of shaped articles is that the individual layers do not adhere to each other sufficiently, which can lead to delamination.

The known slips fail to satisfy the above-named requirements. The object of the invention is therefore to provide light-curing ceramic slips for the stereolithographic preparation of ceramic shaped parts, which display a good stereolithographic processability, result in sufficiently strong and dimensionally stable green bodies and, after debinding and sintering, lead to defect-free, high-strength ceramics. In particular, delamination is to be prevented.

SUMMARY

This object is achieved according to the invention by slips based on radically polymerizable binder, polymerization initiator and filler which comprise the following components:
A) 1 to 30 wt.-% of at least one acidic monomer of general formula I Formula I in which
X is not present or is an (a+b)-valent, substituted or unsubstituted, straight-chained aliphatic residue with at least 2, preferably 3 to 15 carbon atoms, a branched aliphatic residue with at least 3, preferably 3 to 15 carbon atoms, a cycloaliphatic, bi- or tricylic or aromatic residue with 6 to 20, preferably 6 to 15 carbon atoms or a combination of these residues, preferably is an aromatic or cycloaliphatic $C_6$ residue and in particular is a straight-chained or branched aliphatic $C_3$-$C_{15}$ residue, particularly preferably a $C_3$-$C_8$ residue, wherein these groups can contain 1 or more ether groups;

PG is a radically polymerizable group, preferably a vinyl ($CH_2$=CH—), allyl ($CH_2$=CH—$CH_2$—), allyl ether ($CH_2$=CH—$CH_2$—O—), styryl ($CH_2$=CH-phenyl), (meth)acrylate ($CH_2$=C(—H/—$CH_3$)—CO—O—) or (meth)acrylamide group ($CH_2$=C(—H/—$CH_3$)—CO—NH— or $CH_2$=C(—H/—$CH_3$)—CO—NR— with R=$C_1$-$C_4$ alkyl), particularly preferably a (meth)acrylate or (meth)acrylamide group and quite particularly preferably an acrylate ($CH_2$=CH—CO—O—) or acrylamide group ($CH_2$=CH—CO—NH—);

HG is —COOH—, —PO(OH)$_2$, —O—PO(OH)$_2$ or —SO$_3$H, preferably —COOH;

Y is not present or is a divalent, straight-chained aliphatic group with 2 to 40 carbon atoms, a branched aliphatic group with 3 to 40 carbon atoms or a cycloaliphatic or aromatic group with 5 to 40 carbon atoms, wherein Y can contain one or more ether, thioether, amide and/or ester groups, preferably a straight-chained aliphatic residue with 2 to 10 carbon atoms, a branched aliphatic residue with 3 to 12 carbon atoms, a cycloaliphatic, bi- or tricylic or aromatic residue with 6 to 15 carbon atoms or a combination of these residues;

Z is not present or is a divalent, straight-chained aliphatic group with 2 to 40 carbon atoms or a branched aliphatic group with 3 to 40 carbon atoms, wherein Z can contain one or more ether, thioether, amide and/or ester groups, preferably a straight-chained aliphatic residue with 2 to 10 carbon atoms, a branched aliphatic residue with 3 to 12 carbon atoms, a cycloaliphatic, bi- or tricylic or aromatic residue with 6 to 15 carbon atoms, a combination of these residues or an oligoethylene glycol (—($CH_2$—$CH_2$—O)$_n$—, n=1-5) or an oligopropylene glycol residue (—(CH($CH_3$)—$CH_2$—O)$_n$—, n=1-5);

a is an integer from 1 to 5, preferably 1, 2 or 3; and
b is 1 or 2, preferably 1;

A2) 0 to 50 wt.-% of at least one non-acidic radically polymerizable monomer;
B) 0.001 to 2.0 wt.-% photoinitiator; and
C) 30 to 90 wt.-% ceramic and/or glass ceramic particles;
in each case relative to the total mass of the slip.

The ester groups optionally present in Y and/or Z preferably have 1 to 4 carbon atoms. The amide nitrogen of the (meth)acrylamide groups can be substituted by alkyl, preferably $C_1$-$C_3$ alkyl.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

The slips according to the invention comprise, as radically polymerizable binder, at least one acidic monomer according to general formula (I) (component A), preferably a mixture of at least one acidic monomer and at least one non-acidic monomer (component A2). In the following, the acidic monomer is also referred to as adhesive monomer and the non-acidic monomer as comonomer.

It was surprisingly found that the slips according to the invention have only a low polymerization shrinkage and thus allow the preparation of dimensionally stable, flexible green bodies with good dimensional stability and low deformation stress. The slips result in defect-free green bodies which are characterized by an excellent adhesion between the individual stereolithographically produced layers. After debinding and sintering of the green bodies, high-strength ceramic or glass ceramic shaped parts are obtained which are suitable in particular for dental purposes. Furthermore, it was very surprisingly shown that monofunctional adhesive monomers of formula (I) also have an exceptionally high radical photopolymerization activity. By monofunctional monomers are meant monomers with one radically polymerizable group and by multifunctional monomers are meant monomers with two or more radically polymerizable groups. Monomers with two or more radically polymerizable groups effect a cross-linking and are therefore also called cross-linking monomers.

Monomers that contain COOH groups can be obtained e.g. by stoichiometric addition of hydroxyalkyl (meth)acrylates or N-(hydroxyalkyl) (meth)acrylamides to aliphatic, cycloaliphatic, bi- or tricyclic or aromatic di-, tri- or tetracarboxylic acid anhydrides. Anhydrides of dicarboxylic acids are preferred. Hydroxyalkyl (meth)acrylates or N-(hydroxyalkyl) (meth)acrylamides suitable for this are for example 2-hydroxyethyl (meth)acrylate, 2-hydroxypropyl (meth)acrylate, 4-hydroxybutyl(meth)acrylate, 10-hydroxydecyl (meth)acrylate, OH-terminated poly(ethylene glycol) or poly(propylene glycol) mono(meth)acrylate, α-hydroxymethylacrylic acid ethyl ester, N-(2-hydroxyethyl)(meth)acrylamide, N-methyl-N-(2-hydroxyethyl)acrylamide, N-(5-hydroxypentyl)(meth)acrylamide or N-(10-hydroxy-decyl)(meth)acrylamide. Preferred dicarboxylic acid anhydrides are succinic, maleic, fumaric acid or glutaric anhydride, cyclohexane-1,2-dicarboxylic acid anhydride, 1,2-cyclopropanedicarboxylic acid anhydride, norbornene-2,3-dicarboxylic acid anhydride, the Diels-Alder adduct of maleic anhydride and 1,3-cyclopentadiene or phthalic anhydride. Furthermore, COOH-containing monomers can be synthesized by ring-opening addition of di- or higher functionalized carboxylic acids, such as oxalic, malonic, succinic, glutaric, adipic, sebacic, pimelic, suberic, maleic, terephthalic, isophthalic, phthalic, cyclohexane dicarboxylic, gallic, tartaric, or citric acid to e.g. glycidyl (meth)acrylate or 4-vinyl-1-cyclohexene 1,2-epoxide or are obtainable as half-esters by esterification of the above-mentioned hydroxyalkyl (meth)acrylates or N-(hydroxyalkyl) (meth)acrylamides with the listed dicarboxylic acids.

Examples of suitable acidic polymerizable phosphoric acid esters (HG=—O—PO(OH)$_2$) are 2-methacryloyloxypropyldihydrogen phosphate, 2-methacryloyloxyethyldihydrogen phosphate, 10-methacryloyloxydecyldihydrogen phosphate, 6-(methacrylamido)hexyldihydrogen phosphate and 1,3-bis-(N-acryloyl-N-propyl-amino)-propan-2-yl-dihydrogen phosphate.

Examples of suitable phosphonic acid monomers (HG=—PO(OH)$_2$) are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid or 2-[4-(dihydroxyphosphoryl)-2-oxa-butyl]-acrylic acid.

Examples of suitable polymerizable sulphonic acids (HG=—SO$_3$H) are vinyl sulphonic acid, 4-vinylphenyl sulphonic acid or 3-(methacrylamido)propyl sulphonic acid.

Preferred are monomers that contain COOH groups (HG=COOH), and above all reaction products of hydroxyalkyl acrylates, such as hydroxyethyl or hydroxypropyl acrylate, with aliphatic, cycloaliphatic or aromatic carboxylic acid anhydrides, in particular with succinic, glutaric, cyclohexane-1,2-dicarboxylic acid or phthalic anhydride.

Particularly preferred are monomers with COOH groups (HG=COOH) which have vinyl, allyl, allyl ether, styryl, (meth)acrylate or (meth)acrylamide groups as polymerizable group(s) PG, in particular (meth)acrylate or (meth)acrylamide residues, wherein acrylate or acrylamide residues are quite particularly preferred.

Particularly preferred are monomers according to formula (I) in which the variables independently of each other have the following meanings:

X is not presently or is an (a+b)-valent, unsubstituted, branched or straight-chained aliphatic residue with 3 to 15, preferably 3 to 8 carbon atoms, which can contain 1 or 2 ether groups;
PG is an acrylate or acrylamide group,
HG is —COOH,
Y is a divalent, straight-chained aliphatic group with 2 to 8 carbon atoms or a branched aliphatic group with 3 to 8 carbon atoms, wherein these groups can contain 1 ester group, and
Z is a divalent, straight-chained aliphatic group with 2 to 10 carbon atoms or a branched aliphatic group with 3 to 10 carbon atoms, wherein these groups can contain 1 or more, preferably 0 to 3, ether groups,
a is 1, 2 or 3, and
b is 1.

According to the invention, monomers of formula (I) in which all the variables have one of the preferred or particularly preferred meanings are particularly preferred.

The radically polymerizable binder preferably comprises at least one non-acidic monomer A2. In the radically polymerizable resins, mono- or multifunctional (meth)acrylates, (meth)acrylamides, vinyl monomers or mixtures thereof can in particular be used as non-acidic comonomers. Examples of (meth)acrylates are ethyl, hydroxyethyl, hydroxypropyl, butyl, benzyl, tetrahydrofurfuryl or isobornyl (meth)acrylate, bisphenol-A-di(meth)acrylate, bis-GMA (an addition product of methacrylic acid and bisphenol-A-diglycidyl ether), addition products of 2-hydroxyalkyl (meth)acrylate and diisocyanates, such as hexamethylene diisocyanate or 2,2,4-trimethylhexamethylene diisocyanate, di-, tri- or tetraethylene glycol di(meth)acrylate, (meth)acrylate-terminated poly(ethylene glycols) or poly(propylene glycols), trimethylolpropane tri(meth)acrylate, pentaerythritol tetra(meth)acrylate, as well as glycerol di- and tri(meth)acrylate, 1,4-butanedioldi(meth)acrylate, 1,10-decanedioldi(meth)acrylate or 1,12-dodecanedioldi(meth)acrylate.

Preferred examples of (meth)acrylamides are N-ethyl acrylamide, N,N-dimethacrylamide, N-(2-hydroxyethyl) acrylamide, N-methyl-N-(2-hydroxyethyl)acrylamide, N-ethyl methacrylamide or N-(2-hydroxyethyl)methacrylamide, N,N'-diethyl-1,3-bis(acrylamido)propane, 1,3-bis (methacrylamido)propane, 1,4-bis(acrylamido)-butane or 1,4-bis(acryloyl)piperazine. Suitable vinyl monomers are N-vinylpyrrolidone or vinyl acetate.

The slips according to the invention preferably comprise less than 40 wt.-% and particularly preferably less than 20 wt.-% cross-linking monomers relative to the total mass of radically polymerizable components.

The ceramic slips or glass ceramic slips according to the invention can comprise, as components B, the known radical photoinitiators (cf. J. P. Fouassier, J. F. Rabek (ed.), Radiation Curing in Polymer Science and Technology, vol. II, Elsevier Applied Science, London and New York 1993, which is hereby incorporated by reference) for the visible range, such as acyl or bisacyl phosphine oxides, titanocene photoinitiators, such as bis($\eta^5$-cyclopentadienyl)bis[2,6-difluoro-3-(1H-pyrr-1-yl)phenyltitanium or bis($\eta^5$-methylcyclopentadienyl)bis[2,3,4,5,6-pentafluorophenyl)-titanium, but above all α-diketones, such as 9,10-phenanthrenequinone or diacetyl, furil, or 4,4'-dialkoxybenzil and camphorquinone. Furthermore, suitable photoinitiators for the visible range are combinations of photoreducible dyes, such as acridine, xanthene, azine or polymethine dyes with accelerators, such as phosphines, sulphinates, enolates or suitable borates (cf. J. V. Crivello, K. Dietliker, Photoinitiators for Free Radical, Cationic & Anionic Photopolymerization, 2nd Ed., In: Surface Coating Technology, Editor: G. Bradley, Vol. III, Wiley & Sons, Chichester etc. 1998, 239 et seq., which is hereby incorporated by reference). Particularly suitable are amine-free Norrish type I photoinitiators which absorb above 400 nm, above all monoacyltrialkyl or diacyldialkyl germanium compounds, such as benzoyltrimethylgermanium, dibenzoyldiethylgermanium or bis(4-methoxybenzoyl)diethylgermanium as well as bisacyl phosphine oxides which all lead to a high polymerization rate even without amine accelerator. Mixtures of the different photoinitiators can also be used, such as mixtures of dibenzoyl diethyl germanium combined with a bisacyl phosphine oxide.

Reducing agents, such as 4-(dimethylamino)-benzoic acid ester, N,N-dimethylaminoethyl methacrylate, N,N-dimethyl-sym.-xylidine or triethanolamine can be used as accelerators for α-diketones. Further accelerators are ascorbic acid, barbiturates or sulphinic acids, which are advantageous above all in combination with suitable peroxides. Moreover, known cationic photoinitiators, such as diaryliodonium or triarylsulphonium salts, can also be used as accelerators.

Photoinitiators are preferably used in an amount of 0.001-2.0 wt.-%, particularly preferably 0.01-1 wt.-%, and accelerators in an amount of 0 to 2.0 wt.-%, particularly preferably 0.01 to 1 wt.-%.

The slips according to the invention comprise as component C ceramic and/or glass ceramic particles.

By ceramics are meant inorganic materials which have a crystalline structure and are usually prepared from corresponding powders. The preparation of the ceramic preferably takes place by sintering (sintered ceramic). Oxide ceramics are preferably obtained by sintering metal oxide powders such as $ZrO_2$ or $Al_2O_3$. In addition, oxide ceramics can also contain one or more glass phases. Glass ceramics are materials which are usually prepared from amorphous glasses, in particular silicate glasses, by controlled crystallization and in which a glass phase and one or more crystal phases are present simultaneously in the solid. In the case of sinterable glass ceramics, both glass powders and glass ceramic powders can be used as a starting material.

Preferred are sinterable glass ceramic particles based on leucite- or lithium disilicate-reinforced glasses and/or ceramic particles based on $ZrO_2$ or $Al_2O_3$, preferably pure $ZrO_2$ or pure $Al_2O_3$, particles based on $ZrO_2$ stabilized with $HfO_2$, $CaO$, $Y_2O_3$, $CeO_2$ and/or $MgO$, particles based on other metal oxides and also ceramic composite materials which are prepared from several oxides and are thus constructed from various crystalline oxide phases, preferably $ZrO_2$—$Al_2O_3$, in particular pure $ZrO_2$—$Al_2O_3$ or $ZrO_2$—$Al_2O_3$ stabilized with $HfO_2$, $CaO$, $Y_2O_3$, $CeO_2$ and/or $MgO$.

The term "pure" is to be understood to mean "chemically pure", i.e. a $ZrO_2$ or $Al_2O_3$ ceramic is constructed only from $ZrO_2$ or $Al_2O_3$ respectively. In addition to the base oxide such as $ZrO_2$ or $Al_2O_3$, stabilized ceramics contain a stabilizer which is preferably selected from $HfO_2$, $CaO$, $Y_2O_3$, $CeO_2$, $MgO$ and mixtures thereof. The stabilizer is preferably used in a quantity of 3 to 5 wt.-%, relative to the mass of the stabilized ceramic. High-strength $ZrO_2$ ceramics preferably contain 3 to 5 wt.-% $Y_2O_3$ (yttrium oxide) to stabilize the tetragonal crystal structure. This $ZrO_2$ ceramic is referred to as Y-TZP (yttrium-stabilized tetragonal zirconium dioxide polycrystals). Ceramic particles which comprise only base oxide and stabilizer are particularly preferred.

The above-mentioned ceramic and glass ceramic particles are suitable in particular for dental applications. In addition, particles of non-oxide ceramics can also be used in particular for non-dental purposes. Preferred non-oxide ceramics are carbides, above all silicon carbide or boron carbide, nitrides, in particular silicon, aluminium or boron nitride, borides and/or silicides.

The particle size of component C is preferably in the range from 20 nm to 50 µm. It depends on the ceramic used. In the case of $Al_2O_3$, the size of the particles used as component C is preferably in the range from 20 to 5000 nm, particularly preferably between 75 and 200 nm; in the case of glass ceramic in the range from 100 nm to 50 µm, quite preferably between 0.1 and 10 µm; in the case of Y-TZP zirconium dioxide in the range from 20 to 5000 nm, quite preferably between 50 and 3500 nm. The particle size is preferably chosen such that sedimentation-stable slips are obtained. The particle sizes are the absolute upper and lower limits.

Furthermore, ceramic or glass ceramic particles with a particle size in the range from 10-200 nm can also be used as nano- or organosols, i.e. as a dispersion of the nanoparticles in a solvent, a suitable monomer of component A or a mixture thereof.

In a preferred embodiment of the invention, the particles are surface-modified with suitable substances. Compounds which are chemically bound, i.e. by ionic or covalent bonds, to the surface of the ceramic or glass ceramic particles are preferably used for the surface modification. Compounds which contain either acid groups, preferably carboxylic acid, phosphonic acid, hydrogen phosphate groups or acidic phosphoric acid ester groups, or silyl groups, preferably alkoxysilyl groups, are preferred. The particle surface can be partially or preferably completely covered with the modification agent. The modification agents used according to the invention are monomeric compounds.

Compounds which, unlike the so-called adhesion promoters or coupling reagents, contain groups only reacting with the particle surface but not polyreactive groups such as radically polymerizable groups, e.g. (meth)acryl, (meth)acrylamide, vinyl, vinyl ether or epoxide groups which form a covalent bond with the resin matrix (A), are particularly suitable according to the invention. Such compounds are referred to as non-polymerizable surface modifiers herein. These compounds have the advantage that a stable bond does not form between the ceramic particle surface and the polymer matrix in the cured green body, which simplifies the complete removal of the polymer portions in the debinding process.

Linear or branched carboxylic acids, such as formic acid, acetic acid, propionic acid, octanoic acid, isobutyric acid, isovaleric acid, pivalic acid, acidic phosphoric acid esters, such as dimethyl, diethyl, dipropyl, dibutyl, dipentyl, dihexyl, dioctyl or di(2-ethylhexyl)phosphate, or phosphonic acids, such as methyl, ethyl, propyl, butyl, hexyl, octyl or phenyl phosphonic acid, are particularly suitable as non-polymerizable surface modifiers. Silanes suitable as non-polymerizable surface modifiers are for example propyltrimethoxysilane, phenyltrimethoxysilane, hexyltrimethoxysilane, octyltrimethoxysilane, trimethylchlorosilane, trimethylbromosilane, trimethylmethoxysilane or hexamethyldisilazane.

According to a preferred embodiment, the slips according to the invention comprise as component D an inhibitor as stabilizer to prevent a spontaneous polyreaction. The inhibitors or stabilizers improve the storage stability of the slips and also prevent an uncontrolled polyreaction in the stereolithographic tank. The inhibitors are preferably added in such an amount that the slips are storage-stable over a period of about 2-3 years. The inhibitors are preferably used in an amount of 0.001 to 1.0 wt.-%, particularly preferably 0.001 to 0.50 wt.-%, in each case relative to the total mass of the slip.

Phenols such as hydroquinone monomethyl ether (MEHQ) or 2,6-di-tert-butyl-4-methyl-phenol (BHT), which are really effective only in the presence of oxygen and are usually employed in a concentration range from 200-2000 ppm are used as so-called aerobic inhibitors for radical reaction resins. Anaerobic inhibitors, such as phenothiazine, 2,2,6,6-tetramethyl-piperidine-1-oxyl radical (TEMPO), iodine, copper(I) iodide, on the other hand, are effective in smallest concentrations (10-50 ppm) even in the absence of oxygen. A polymerisation normally takes place only when these additives are consumed. It is often also advantageous to use a mixture of aerobic and anaerobic inhibitors.

Aerobic inhibitors are preferably used in an amount of 0.01 to 0.50 wt.-% and anaerobic inhibitors in an amount of 0.001 to 0.02 wt.-%, each relative to the total mass of the slip. Preferred mixtures comprise 0.02 to 0.2 wt.-%, in particular 0.01 to 0.10 wt.-% aerobic inhibitors and/or 0.001 to 0.01 wt.-% anaerobic inhibitors, again relative to the total mass of the slip.

Furthermore, to avoid scattering effects or to adjust the through-curing depth, suitable dyes can be added which absorb above all in the wavelength range of the photoinitiators or sensitizers used, above all azo and acridine dyes. Specific examples of these are 2,4-dihydroxy-4-nitroazobenzene, Sudan Yellow 146, Sudan Orange 220, Sudan M Red 380, Sudan Yellow 177 liquid. Finally, organic white pigments or matting agents, such as e.g. based on PE waxes, polyamide 12 or polymethyl urea resins, can also be used to avoid scattering effects or to adjust the through-curing depth. The absorption of the slip can be influenced in a controlled manner (reduced) by the mentioned dyes and the over-radiation caused by scattering effects or too small an absorption of the slip can thereby be minimized. Scattering and over-radiation can have a disadvantageous effect on the shape fidelity of the stereolithographically prepared component.

According to a further preferred embodiment of the invention, the slips comprise a so-called debinding accelerator as component E. This is preferably used in an amount of 0 to 20 wt.-%, particularly preferably 0.01 to 10 wt.-%, in each case relative to the total mass of the slip. By debinding accelerators are meant substances which facilitate the removal of the binder during the debinding process.

The debinding of the green compact can be promoted or influenced in targeted manner by suitable, i.e. polyreactively effective, substances in the polyreaction resin. On the one hand, these are additives which influence the network formation, such as in particular chain-transfer-active substances, so-called chain transfer agents, which result in a reduction in the polymer network density and thus in a better thermal decomposability. Known chain transfer agents e.g. for radical polymerization are in particular mercaptans, such as e.g. lauryl mercaptan, and disulphides. Disulphides, in particular dithiourethane disulphides, such as tetramethyl-thiuram disulphide or isopropylxanthogenic acid disulphide, act as so-called photoiniferters in radical photopolymerization. These are compounds which both act as photoinitiator (photoini-) and participate in transfer reactions (-fer-) and termination reactions (-ter-) (cf. T. Otsu, M. Yoshida, Makromol. Chem., Rapid. Commun. 3 (1982) 127-132: Role of Initiator-Transfer Agent-Terminator (Iniferter) in Radical Polymerizations: Polymer Design by Organic Disulfides as Iniferters, which is hereby incorporated by reference). The addition of chain-transfer-active substances, i.e. chain transfer agents or photoiniferters, effects a reduction of the network density of the polyreaction network with a virtually unchanged reactivity of the polyreaction resin mixture. Chain transfer agents and photoiniferters are preferably used in an amount of 0.005 to 2 wt.-% each and particularly preferably 0.01 to 1.0 wt.-%, relative to component (A).

According to the invention, comonomers which result in a reduction in the thermal stability of polymer networks can advantageously also be used as debinding accelerators. Comonomers which contain thermally labile groups, such as peroxide, azo or urethane groups, which are incorporated into the polymer network during the stereolithographic process and then accelerate the degradation of the polymer network in the thermal debinding process are suitable for this. A preferred example of a polymerizable peroxide is 4,4'-divinyl benzoyl peroxide which can be obtained by reaction of 4-vinyl benzoyl chloride with sodium peroxide. A preferred example of a polymerizable azo compound is the ester from 2-hydroxyethyl methacrylate and 4,4'-azobis-(4-cyanovaleric acid). Preferred thermally labile urethanes can be obtained from diisocyanates, for example by reaction of 2,2,4-trimethylhexamethylene diisocyanate (TMDI) or toluoylene diisocyanate (TDI) with hydroxypropyl acrylate (HPA) or 2-hydroxyethyl acrylate (HEA). A further example of a thermally labile monomer building block is α,α,α',α'-tetramethyl-1,4-benzene-dimethyl acrylate, the incorporation of which into a Michael addition network for example of diacrylates and diacetoacetates in the presence of catalytic acid quantities leads to an accelerated decomposition of the polymer network.

Moreover, comonomers the polyreaction products of which are readily thermally degradable are suitable as debinding accelerators. Comonomers which, like α-methylstyrene, have a low ceiling temperature $T_c$ are preferred for radical polymerization resins. The ceiling temperature is the limit temperature at which the polymerization is in equilibrium with the depolymerization, and can be calculated from the quotient of the polymerization enthalpy and the polymerization entropy (cf. H.-G. Elias, Makromoleküle, vol. 1, $6^{th}$ Edition, Wiley-VCH, Weinheim etc. 1999, 193 et seq., which is hereby incorporated by reference). For example, $T_c$ is 61° C. for α-methylstyrene. The ceiling temperature $T_c$ of polytetrahydrofuran (PTHF) is 80° C. Accordingly, the decomposability of poly(meth)acrylate networks can be accelerated e.g. by using telechels with radically polymerizable groups as comonomer, in particular PTHF di(meth)acrylate telechels. According to the invention, comonomers with a ceiling temperature of −10 to 150° C., preferably 10 to 150° C. and particularly preferably 20 to 130° C. are particularly suitable. The comonomers are preferably used in an amount of 0.1 to 30 wt.-% and particularly preferably 0.5 to 20 wt.-%, relative to component (A).

The slips according to the invention preferably comprise a coloring component as component F. The coloring component is preferably used in an amount of 0.00001 to 2.0 wt.-%, particularly preferably 0.001 to 1.0 wt.-% and quite particularly preferably 0.01 to 0.5 wt.-%, relative to the mass of component C.

The customary dyes or pigments are not suitable as coloring component according to the invention, since they are not stable enough to survive the debinding or sintering process. According to the invention, reactive transition metal compounds are used as component F which on the one hand are soluble in binder A and do not adversely affect the course of the photocuring and which on the other hand form coloring transition metal ions during the debinding of the stereolithographically prepared ceramic green compact or the sintering of the ceramic white body obtained therefrom. Transition metal compounds preferred as coloring component are in particular acetylacetonates or carboxylic acid salts of the elements iron, cerium, praseodymium, terbium, lanthanum, tungsten, osmium, terbium and manganese. The salts of the carboxylic acids acetic, propionic, butyric, 2-ethylhexylcarboxylic, stearic and palmitic acid are preferred. Above all the corresponding Fe, Pr, Mn and Tb compounds, such as iron (III) acetate or acetyl acetonate, manganese (III) acetate or acetyl acetonate, praseodymium (III) acetate or acetyl acetonate or terbium (III) acetate or acetyl acetonate as well as the corresponding carboxylic acid salts are particularly preferred.

The coloring components are preferably chosen such that tooth-coloured ceramic shaped parts are obtained after the debinding and sintering.

The transition metal compounds used as component F are incorporated (usually as ions) into the structure as coloring component and influence the colour of the sintered bodies after the sintering process. In contrast to this, the previously mentioned organic dyes serve to adjust the through-curing depth of the slips. These are decomposed completely during the debinding and sintering.

According to the invention, those slips are preferred which, in addition to the components A, B and C, comprise an inhibitor D, a debinding accelerator E and/or a coloring component F. Particularly preferred are slips which comprise the components A, B, C and D; A, B, C and E; A, B, C and F, quite particularly preferred are slips which comprise the components A, B, C, D and E; A, B, C, D and F; A, B, C, E and F, and in particular slips which comprise the components A, B, C, D, E and F. It is preferred in each case to use the above-defined components and preferred components preferably in the above-mentioned amounts.

In addition to the components A to F, the slips according to the invention can comprise further components as additives.

For example, the slips according to the invention can comprise one or more dispersants which prevent the formation of agglomerates and the depositing of the ceramic particles. Suitable dispersants for ceramic slips are above all polymers such as polycarboxlic acids, polycarboxylic acid salts or non-ionic polymers, such as polyethylene glycol or carboxy-methylcellulose. In particular suitable as dispersants are polymers which are soluble in the polyreaction resin. For example poly(meth)acrylates which are soluble in light-curable (meth)acrylate resins, wherein the achievable solids content normally decreases as the molar mass and content of these polymers in the slip increase. Furthermore, the particles of component C can even be pre-treated with the dispersants before the preparation of the slips. Dispersants are preferably used in an amount of 0 to 5 wt.-% and particularly preferably 0.5 to 3.0 wt.-%, relative to the total mass of the slip.

The ceramic slips according to the invention can comprise, as further components, one or more plasticizers which prevent the ceramic green compact from becoming brittle after the photochemical hardening and a possible drying. In addition, plasticizers ensure a sufficient flexibility. Typical plasticizers are phthalates, such as dibutyl or dihexyl phthalate, non-acidic phosphates, such as tributyl or tricresyl phosphate, n-octanol, glycerol or polyethylene or polypropylene glycols or corresponding ester or ether derivatives. Plasticizers are preferably used in an amount of 0 to 20 wt.-% and particularly preferably 0 to 10 wt.-%, relative to the total mass of radically polymerizable components.

Furthermore, the slips according to the invention can advantageously also comprise a solvent. For example the compounds mentioned above as plasticizers are suitable as solvents.

Components which have a boiling point of at least about 120° C. and a relatively high evaporation enthalpy are preferably used as solvents, with the result that there is no premature evaporation during the stereolithographic processing of the slip. Particularly preferred are solvents with a boiling point of 150 to 250° C., quite particularly preferably of 180 to 230° C. Particularly suitable are 1-octanol, 1- or 2-nonanol, diethylene glycol diethyl ether, 2,5-dimethoxytetrahydrofuran, oxalic acid dibutyl ester, cyclohexanol, polypropylene glycol diacetate, cyclohexanone, acetoacetic acid ethyl ester and mixtures thereof. The solvent or solvents are preferably used in an amount of 0 to 70 wt.-%, particularly preferably 10 to 50 wt.-%, relative to the total mass of radically polymerizable components.

Mixtures of compounds which can be progressively evaporated in a temperature range between 150 and 250° C. are particularly suitable as plasticizers and/or solvents. Progressively evaporated means here that mixtures of one or more plasticizers and/or one or more solvents which have different boiling points are used, with the result that these components can be evaporated in succession, preferably in a temperature range from 150° C. to 250° C., and can thus be removed in a way that treats the shaped parts much more carefully.

The evaporation of the solvents can favour the debinding of the polymer portions taking place at increased temperature. It was found that the evaporation of the above solvents leads to the formation of micropores in the green compact which close again upon sintering but which make possible the escape of the gases in the debinding step and thus prevent the formation of stresses and cracks. Moreover, the danger of a separation of the stereolithographically produced layers is reduced and a complete removal of the organic components is made easier.

Alternatively, a porosity of the green body can also be achieved by removing by extraction elutable portions before heat treatment. Suitable extractable components are water-soluble polymers, such as polyvinyl alcohol, polyvinyl pyrrolidone and polyethylene glycols. Furthermore, petrol-soluble substances such as paraffins or waxes and long-chained fatty acid esters can be used. The preferred amount of extractable components in the resin matrix is between 0 and 40 wt.-%, particularly preferably between 0.1 and 30 wt.-%, relative to component (A).

In addition, the slips according to the invention can comprise defoaming and/or antiskinning agents which prevent foaming during the preparation of the slips or the formation of a skin during the processing of the slips. Defoaming and/or antiskinning agents are preferably used in each case in an amount of 0 to 5 wt.-% and particularly preferably 0.1 to 2 wt.-% in the organic matrix, relative to the mass of component (A).

Slips which comprise the above-mentioned components in the following quantities are particularly preferred according to the invention:

Component A: 1 to 30, preferably 5 to 20 wt.-%
Component A2: 0 to 20, preferably 0 to 10 wt.-%
Component B: 0.001 to 2, preferably 0.01 to 1.0 wt.-%
Component C: 30 to 90, particularly preferably 35 to 85 and quite particularly preferably 40 to 85 wt.-%
Solvent and/or plasticizer 0 to 30, preferably 0 to 15 wt.-%

The rheological properties of the slips according to the invention are preferably adjusted such that their viscosity is in the range from 0.02-20000 Pa·s, particularly preferably 0.05-5000 Pa·s. It is advantageous if there are no yield points if at all possible. The viscosity and the yield points are determined at 23° C. with a plate-plate viscometer.

The slips according to the invention are particularly suitable for the preparation of ceramic or glass ceramic shaped articles in particular for the preparation of dental restorations, such as inlays, onlays, veneers, crowns, bridges or frameworks.

A subject of the invention is also a process for the preparation of ceramic or glass ceramic shaped articles, wherein
(a) a green body is prepared by curing a slip according to the invention by local introduction of radiation energy with formation of the geometric shape of the green body,
(b) the green body is then subjected to a heat treatment to remove the binding agent (debinding), in order to obtain a white body, and
(c) the white body is then sintered.

The preparation of the green body in step (a) takes place by rapid prototyping, preferably by stereolithography. A ceramic green body, which is debound in step (b), is prepared through layer-by-layer radiation curing of a free-flowing ceramic slip. The binder used is removed by heating the green body to a temperature of preferably 90° C. to 600° C., and the so-called white body is obtained. The white body is sintered in step (c) to form a dense ceramic shaped article. The sintering of the white body takes place in the sintering furnace, preferably at a temperature of 650 to 1100° C., preferably 700 to 900° C., for glass ceramic, 1100 to 1600° C., preferably 1400 to 1500° C., for zirconium dioxide, and 1400 to 1800° C., preferably 1600 to 1700° C., for aluminium oxide. The ceramic shaped articles prepared according to the process according to the invention are characterized by a high strength and great accuracy of detail. The bending strength according to ISO 6872 is preferably more than 100 MPa, in particular in the range from 150 to 500 MPa, for shaped articles made of glass ceramic. Shaped articles made of $Al_2O_3$ have a bending strength of preferably more than 300 MPa, in particular from 500 to 700 MPa and shaped articles made of $ZrO_2$ of over 500 MPa, in particular from 800 to 1100 MPa.

The invention is explained in more detail below by means of drawings and examples.

Figure 1:
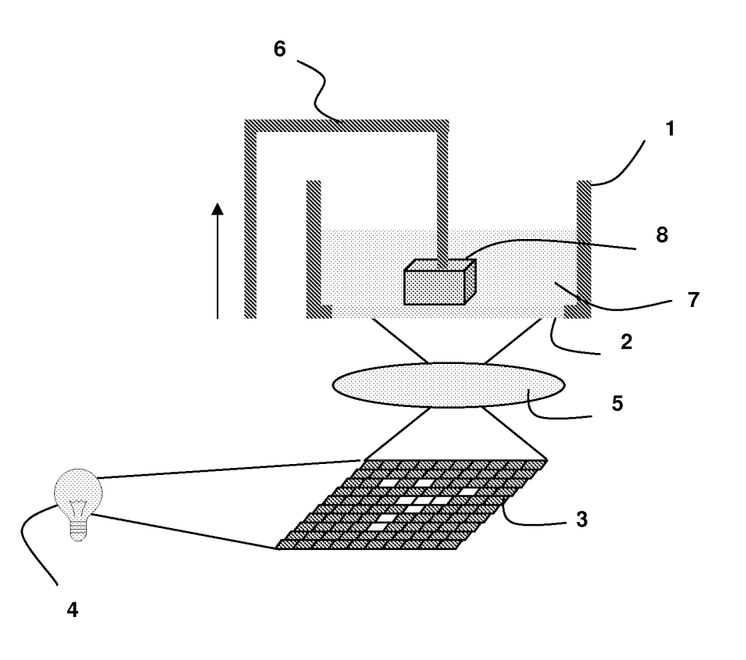
FIG. 1 shows a schematic representation of a device for carrying out the process according to the invention.

As FIG. 1 shows, the device comprises a container 1 for the slip 7 according to the invention. The container 1 is also referred to as a polymerization tank or tank. In the embodiment shown, the tank 1 has a transparent window 2 through which the slip is selectively irradiated and cured from below. Arranged underneath the tank 1 is a computer-controlled, movable mirror 3, a so-called micro-mirror array, which is irradiated with a radiation source 4. The image of the mirror 3 is projected onto the transparent window 2 by an optical device 5. Arranged above the tank 1 is a substrate carrier 6 movable in Z direction which carries the body 8 constructed in layers. The substrate carrier 6 can have a carrier plate, not shown here. The substrate carrier 6 is immersed in the slip until the distance between the carrier 6 or the body 8 attached thereto and the inner surface of the tank 1 corresponds to the layer thickness of the layer to be produced. The slip layer between carrier 6 and inner tank surface is then selectively irradiated and cured through the transparent window 2 with the help of the mirror 3. Cured areas form which adhere to the carrier 6. The carrier 6 is then raised in Z direction, with the result that a slip layer with the desired thickness forms again between the adhering layer and the inner tank surface. This layer is also selectively cured by irradiation and the desired shaped articles, preferably a dental restoration, is constructed in layers by repeating the process.

EXAMPLES

Example 1

Light-Curing Ceramic Slips and Stereolithographically Produced Shaped Articles

To prepare the ceramic slips, the monomers listed in the following table (PS-m-HEA=reaction product of 1 mol phthalic acid anhydride with 1 mol 2-hydroxyethyl acrylate; NK-ester CBX-1N=pentaerythritol triacrylate monophthalate 70%), the solvents PEG-400 and PPG-400 respectively and a dispersant were introduced and homogeneously mixed. The photoinitiator K-69 (bis(4-methoxybenzoyl)diethylgermanium, Ivoclar Vivadent AG) or Irgacure 819 (bis(2,4,6-trimethylbenzoyl)phenylphosphine oxide, Ciba SC) was then added and dissolved in the mixture by simple stirring. Finally, the zirconium oxide powder TZ-3YS-E (Tosoh) was added portionwise and dispersed. Free-flowing, homogeneous, stable slips with a filler level of about 37% by volume formed.

Biaxial testpieces were manufactured generatively with the slips A and B using a SL device. The testpieces were cleaned and then sintered.

The sintered biaxial plates were prepared and measured according to ISO 6872:2008. For the slips A and B ceramic shaped articles with a biaxial strength of 1043 and 1055 MPa respectively resulted.

| Component | A [wt.-%] | B [wt.-%] |
| --- | --- | --- |
| Dispersant | 1.00 | 1.00 |
| PS-m-HEA | 12.00 | 11.00 |
| NK-ester CBX-1N | — | 1.00 |
| PEG 400 | 9.95 | — |
| PPG 400 | — | 9.75 |
| K-69 | 0.05 | — |
| Irgacure 819 | — | 0.25 |
| TZ-3YS-E Tosoh | 77.00 | 77.00 |
| Total | 100.00 | 100.00 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A process for the preparation of a ceramic or glass ceramic shaped article comprising: preparing a slip comprising:

A) 1 to 30 wt.-% of at least one acidic monomer of general formula I

Formula I in which
- X is not present or is an (a+b)-valent, unsubstituted, straight-chained or branched aliphatic residue with 3 to 15 carbon atoms, which residues can contain one or two ether groups,
- PG is an acrylate or acrylamide group;
- HG is —COOH;
- Y is a divalent, straight-chained aliphatic group with 2 to 8 carbon atoms, a branched aliphatic group with 3 to 8 carbon atoms or a cycloaliphatic or aromatic group with 6 to 15 carbon atoms, wherein these groups can contain one ester group;
- Z is a divalent, straight-chained aliphatic group with 2 to 10 carbon atoms or a branched aliphatic group with 3 to 10 carbon atoms, wherein these groups can contain one or more ether;
- a is an integer from 1 to 3; and
- b is 1 or 2;

A2) 0 to 50 wt.-% of at least one non-acidic radically polymerizable monomer;
B) 0.001 to 2.0 wt.-% photoinitiator; and
C) 30 to 90 wt.-% ceramic and/or glass ceramic particles;
in each case relative to the total mass of the slip; and
forming a green body through layer-by-layer radiation curing of the slip,
heating the green body to remove binder and form a white body, and
sintering the white body to form a dense ceramic article.

2. The process of claim 1, wherein heating is carried out at a temperature in the range of 90° C. to 600° C.

3. The process of claim 1, wherein sintering is carried out at a temperature in the range of 650 to 1800° C.

4. The process of claim 1, wherein the ceramic or glass ceramic shaped article is a dental restoration.

5. The process of claim 4, wherein the dental restoration comprises an inlay, onlay, veneer, crown, bridge or framework.

6. The process of claim 1, wherein the variables of formula (I) have the following meaning:
- X is not present or is an (a+b)-valent, unsubstituted, branched or straight-chained aliphatic residue with 3 to 15, which residue can contain 1 or 2 ether groups;
- PG is an acrylate or acrylamide group;
- HG is —COOH;
- Y is a divalent, straight-chained aliphatic group with 2 to 8 carbon atoms or a branched aliphatic group with 3 to 8 carbon atoms, wherein these groups can contain 1 ester group;
- Z is a divalent, straight-chained aliphatic group with 2 to 10 carbon atoms or a branched aliphatic group with 3 to 10 carbon atoms, wherein these groups can contain 1 to 3, ether groups;
- a is 1, 2 or 3; and
- b is 1.

7. The process of claim 1, wherein the slip further comprises
D) 0.001 to 1.0 wt.-% inhibitor, relative to the total mass of the slip.

8. The process of claim 1, wherein the slip further comprises
0 to 20 wt.-% debinding accelerator (E),
0 to 20 wt.-% plasticizer and
0 to 70 wt.-% solvent,
in each case relative to the total mass of radically polymerizable components.

9. The process of claim 1, wherein the slip further comprises
F) 0.00001 to 2.0 wt.-% coloring components, relative to the mass of component (C).

10. The process of claim 1, wherein the slip comprises as component (C) glass ceramic particles or ceramic particles based on pure $ZrO_2$, pure $Al_2O_3$, pure $ZrO_2$—$Al_2O_3$, $ZrO_2$ which is stabilized with $HfO_2$, CaO, $Y_2O_3$, $CeO_2$ and/or MgO, $ZrO_2$—$Al_2O_3$ which is stabilized with $HfO_2$, CaO, $Y_2O_3$, $CeO_2$ and/or MgO or non-oxide ceramics.

11. The process of claim 1, wherein the particles of component (C) are surface-modified with a linear or branched carboxylic acid, an acidic phosphoric acid ester, a phosphonic acid, or a silane, wherein the surface-modification agent does not contain radically polymerizable groups.

12. The process of claim 1, wherein the particles of component (C) have a particle size in the range from 20 nm to 50 µm.

13. The process of claim 8, wherein the slip comprises as debinding accelerator (E)
a chain transfer agent; and/or
a comonomer which has one or more thermally labile groups; and/or
a comonomer with a ceiling temperature of −10 to 150° C.

14. The process of claim 9, wherein the slip comprises as coloring component (F) a transition metal compound.

15. The process of claim 1, wherein the slip further comprises at least one further component from the group of dispersants, defoaming agents, and antiskinning agents.

16. The process of claim 1, wherein the slip comprises at most 40 wt.-% of multifunctional monomers relative to the total mass of radically polymerizable components.

17. The process of claim 6, wherein:
X is an (a+b)-valent, unsubstituted, branched or straight-chained aliphatic residue with 3 to 8 carbon atoms, which residue can contain 1 or 2 ether groups.

18. The process of claim 13, wherein
the chain transfer agent comprises a mercaptan, a disulphide or a photoiniferter; and/or
the comonomer comprises one or more peroxide, azo or urethane groups; and/or
the comonomer comprises α-methylstyrene, polytetrahydrofuran (PTHF), or a telechel with radically polymerizable groups.

19. The process of claim 18, wherein
the chain transfer agent comprises lauryl mercaptan, a dithiourethane disulphide, tetramethyl-thiuram disulphide or isopropylxanthogenic acid disulphide; and/or
the comonomer comprises a PTHF di(meth)acrylate telechel.

20. The process of claim 14, wherein the slip comprises as coloring component (F) an acetyl acetonate and/or a carboxylic acid salt of the elements iron, cerium, praseodymium, terbium, lanthanum, tungsten, osmium, terbium and manganese.

21. The process of claim 20, wherein the slip comprises as coloring component (F) iron (III) acetate or iron (III) acetyl acetonate, manganese (III) acetate or manganese (III) acetyl acetonate, praseodymium (III) acetate or praseodymium (III) acetyl acetonate or terbium (III) acetate or terbium (III) acetyl acetonate.

22. The process of claim 11, wherein
- the linear or branched carboxylic acid comprises formic acid, acetic acid, propionic acid, octanoic acid, isobutyric acid, isovaleric acid or pivalic acid;
- the acidic phosphoric acid ester comprises dimethyl, diethyl, dipropyl, dibutyl, dipentyl, dihexyl, dioctyl or di(2-10 ethylhexyl)phosphate;
- the phosphonic acid comprises methyl, ethyl, propyl, butyl, hexyl, octyl or phenyl phosphonic acid; or
- the silane comprises propyltrimethoxysilane, phenyltrimethoxysilane, hexyltrimethoxysilane, octyltrimethoxysilane, trimethylchloro-silane, trimethylbromosilane, trimethylmethoxysilane or hexamethyldisilazane.

\* \* \* \* \*